US00PP23395P3

(12) United States Plant Patent
Austin

(10) Patent No.: US PP23,395 P3
(45) Date of Patent: Feb. 19, 2013

(54) ***ROSA HYBRIDA* SHRUB NAMED 'AUSQUIRK'**

(50) Latin Name: ***Rosa hybrida* shrub**
Varietal Denomination: AUSquirk

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 95 days.

(21) Appl. No.: 13/065,126

(22) Filed: Mar. 14, 2011

(65) Prior Publication Data

US 2012/0096603 P1 Apr. 19, 2012

(30) Foreign Application Priority Data

Oct. 13, 2010 (QZ) ..... PBR 20102154

(51) Int. Cl.
*A01H 5/00* (2006.01)

(52) U.S. Cl. ..... Plt./103

(58) Field of Classification Search ..... Plt./103
See application file for complete search history.

*Primary Examiner* — June Hwu

(74) *Attorney, Agent, or Firm* — Kauth, Pomeroy, Peck & Bailey LLP

(57) ABSTRACT

A variety of rose plant of the shrub class, named 'AUSquirk'. The 'AUSquirk' rose is a plant having rosette-shaped white blooms, very bushy growth, matt green foliage, a long flowering season and being particularly disease resistant.

1 Drawing Sheet

Classification: The present invention relates to a new *Rosa hybrida* shrub.

Variety denomination: The new plant has the varietal denomination 'AUSquirk.'

CROSS-REFERENCE TO RELATED APPLICATIONS

The current application claims priority to a European Community Plant Variety Application No. 2010/2154, filed Oct. 13, 2010, the disclosure of which is incorporated herein by reference.

ORIGIN OF INVENTION

This invention relates to a new and distinct variety of shrub rose plant named 'AUSquirk', which was originated as a sport of the 'AUStilly' variety of *Rosa hybrida,* found on the nursery at David Austin Roses Limited in Albrighton, Wolverhampton, United Kingdom.

BACKGROUND OF THE INVENTION

The primary objective of this breeding was to produce a variety of rose with large rosette-shaped white blooms in the English Rose character with a strong Old Rose fragrance that is particularly disease resistant and winter hardy.

SUMMARY OF THE INVENTION

Among the features which distinguish the new variety from others presently available and commercial rose cultivars known to the inventor is the following combination of characteristics: rosette-shaped white blooms, very bushy growth, matt green foliage, a long flowering season and being particularly disease resistant.

Asexual reproduction of the new variety by budding as performed outdoors at Bowling Green Lane in Albrighton, Britain shows that the foregoing and other distinguishing characteristics come true to form and are established and transmitted through succeeding asexual propagations. 'AUSquirk' may be asexually propagated by budding. The budding successfully occurred on the plant/rootstock *Rosa* 'Dr. Huey' in the United States, as the David Austin Roses nursery in Tyler, Tex.; and *Rosa dumetorum* 'Laxa' for the observed plants in the UK, at the David Austin Roses Limited nursery, Bowling Green Lane, in Albrighton, Wolverhampton.

COMPARISON WITH PARENTS

The parent of this sport is 'AUStilly'. The new rose may be distinguished from its sport parent, by the following combination of characteristics: the new variety is white while the parent is pink.

COMPARISON WITH THE CLOSEST COMMERCIALLY AVAILABLE CULTIVAR

The closest commercially available cultivar to the new variety is the 'AUSlevel' (U.S. Plant Pat. No. 8,765). The new rose may be distinguished from the 'AUSlevel' variety by the following combination of characteristics: the 'AUSquirk' has a bloom form that is a rosette shape, whereas in 'AUSlevel' it is a deep cup, and petals within the blooms of 'AUSquirk' are thinner and more delicate compared with those of 'AUSlevel'. 'AUSquirk' also has a strong old rose fragrance compared with 'AUSlevel's' myrrh fragrance. Finally, 'AUSquirk' has matt green foliage whereas in 'AUSlevel' the foliage is glossy.

BRIEF DESCRIPTION OF ILLUSTRATION

The accompanying photograph illustrates the new variety and shows the flowering thereof from bud to full bloom, on mature and immature stems, depicted in color as nearly correct as it is possible to make in a color illustration of the character for a 1 year-old rose plant. Throughout this specification, color references and/or values are based upon The Colour Chart of The Royal Horticultural Society (2001) except where common terms of color definition are employed.

DESCRIPTION OF THE NEW VARIETY

In the summer of 2005, on the nursery at David Austin Roses Limited in Albrighton, Wolverhampton, United Kingdom, on plant of the *Rosa hybrida* 'AUStilly' grew a stem bearing one white flower. This flower was removed and propagated using the T-budding method onto a *Rosa dumetorum* 'Laxa' rootstock. The following description is of 1 year-old rose plants of the new variety grown outdoors in Albrighton, Britain in the month of August. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

- *Size*.—About 2 cm long and 1.5 cm in diameter when the petals start to unfurl.
- *Form*.—The bud form is pointed ovoid.
- *Color*.—When sepals first divide, the bud color is grayed-green RHS 194D. When half blown, the upper sides of the petals are white RHS 155C, and the lower sides of the petals are white RHS 155C.
- *Calyx*.—Shape: star-shaped. Length: 5 cm. Diameter: 5 cm.
- *Sepals*.—Arrangement: Regular, opening to a star-shape which then folds right back. Color: Upper Surface: green RHS 143C. Lower Surface: green RHS 143C with some red RHS 42C. Length: 2.49 cm. Width: 0.7 cm. Shape: Lanceolate. Margin: Smooth. Surface texture: Upper Surface: Hirsute. Lower Surface: Smooth. Number: There are 3 normally appendaged sepals, and 2 unappendaged sepals with smooth edges.
- *Receptacles*.—Color: green RHS 143C with red RHS 42C. Shape: pitcher. Size: medium, about 0.8 cm×0.8 cm. Surface: Smooth.
- *Peduncle*.—Length: short, averaging about 1.75 cm. Surface: Smooth. Color: grayed-red RHS 182B. Strength: Strong.

Blooms:

- *Size*.—Medium, average open diameter is about 6.5 cm.
- *Borne*.—Several together in small clusters of 6 blooms having flat shape.
- *Stems*.—Strength: Strong, average length is about 16 cm. Diameter: 4 mm.
- *Form*.—When first open, bloom is cupped. Permanence of bloom: all petals curl.

Petalage: Number of petals under normal conditions: 135.

- *Color*.—The upper sides of the petals are white RHS 155C. The reverse sides of the petals are white RHS 155C, and the base of the petals has white RHS 155C.
- *Variegations*.—N/A.
- *Discoloration*.—The general tonality at the end of the first day is white RHS 155C, and at the end of the third day is white 155C.
- *Fragrance*.—Strong. Character of fragrance: Old Rose.

Petals:

- *Texture*.—Smooth.
- *Size*.—Width: 3.75 cm. Length: 3.14 cm.
- *Surface*.—Smooth.
- *Shape*.—Obovate.
- *Margin*.—Weak undulation or reflexing.
- *Apex shape*.—Basically rounded, but some are notched and some are cuspidate.
- *Base shape*.—Pointed.
- *Form*.—Edges slightly quilled.
- *Arrangement*.—Imbricated.
- *Petaloids*.—Number: Few (around 3). Color: white RHS 155C. Length: 8 mm. Width: 3 mm. Shape: Long and thin. Margin: Irregular.
- *Persistence*.—Petals hang on and dry.
- *Lastingness*.—On the plant: Fair, about 5 days. As a cut flower: Not tested.

Reproductive parts:

- *Stamens*.—Number: 18. Length: 4.7 mm.
- *Anthers*.—Length: 0.7 mm. Color: yellow-orange RHS 20A. Arrangement: tucked in calyx or partly so and some mixed with petaloids.
- *Filaments*.—Color: grayed-yellow RHS 160A. Length: 4 mm.
- *Pollen*.—Color: yellow-orange RHS 20A.
- *Pistils*.—Number: 48. Length: 10.2 mm.
- *Styles*.—Color: green-yellow RHS 1C. Length: 10 mm.
- *Stigmas*.—Color: yellow RHS 12B. Length: 0.2 mm.
- *Hips*.—None Observed.

PLANT CHARACTERISTICS

Plant form: Shrub.

Plant growth: Medium, upright and bushy.

Age to maturity: Two years.

Mature plant: Height: 120 cm. Width: 90 cm.

Rootstock: *Rosa* 'Dr. Huey' in the United States, *Rosa dumetorum* 'Laxa' for the observed plants in the UK.

Foliage:

- *Number*.—Leaflets on normal mid-stem leaves is: variable between 5 and 7 (including terminal leaflet).
- *Size*.—Medium, about 14.46 cm long×11.1 cm wide.
- *Quantity*.—Normal. Number of leaves per flowering stem is: 6.
- *Color*.—New foliage: Upper side: green RHS 137C tinged with grayed-red RHS 178A. Lower side: green RHS 137C. Old foliage: Upper side: green RHS 137A. Lower side: green RHS 137C.

Leaflets:

- *Size*.—About 5.74 cm long×3.36 cm wide.
- *Shape*.—Pointed oval.
- *Base shape*.—Obtuse.
- *Apex shape*.—Acute.
- *Texture*.—Leathery.
- *Edge*.—Serrated.
- *Serrations*.—Single.
- *Petiole*.—Color: yellow-green RHS 146C. Length: 4 cm. Width: 0.2 cm. Surface Texture: Smooth.
- *Petiole rachis*.—Color: yellow-green RHS 146C. Underside: with prickles.
- *Stipules*.—Length: 2 cm, smooth. Color: yellow-green RHS 146C with some red-purple RHS 60B.
- *Auricle*.—Shape: Sword-shaped. Length: 6 mm. Width: 3 mm. Color: yellow-green RHS 146C with some red-purple RHS 60B.

*Vein color*.—Same as leaf color.

*Venation pattern*.—Reticulate.

Wood:

*New wood*.—Color: grayed-red RHS 178A. Bark: Smooth.

*Old wood*.—Color: yellow-green RHS 146A. Bark: Smooth.

Branching habit:

*Number*.—10.

*Lateral branch dimensions*.—Length: 40 cm. Width: 4 mm.

Stems:

*Mature stem*.—Length: 62.5 cm. Diameter: 7 mm.

*Internode distance*.—6 cm. The above measurements are all variable, depending on growing conditions in a season.

*Stem pubescence present*.—No.

Prickles:

*Quantity*.—On main canes from base: Ordinary. Number per stem length: 20 per 10 cm. On laterals from main canes: Ordinary. Number per stem length: 15 per 10 cm.

*Form*.—Deep concave.

*Length*.—7 mm.

*Color when young*.—Grayed-purple RHS 183B.

*Color when mature*.—Grayed-orange RHS 175A.

Small prickles:

*Quantity*.—Main stalk: Few. Number per stem length: 10 per 20 cm. Laterals: Few. Number per stem length: 10 per 20 cm.

*Color*.—When young: grayed-purple RHS 183B. When mature: grayed-orange RHS 175A.

Disease resistance:

*Mildew*.—Resistant.

*Blackspot*.—Resistant.

*Rust*.—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

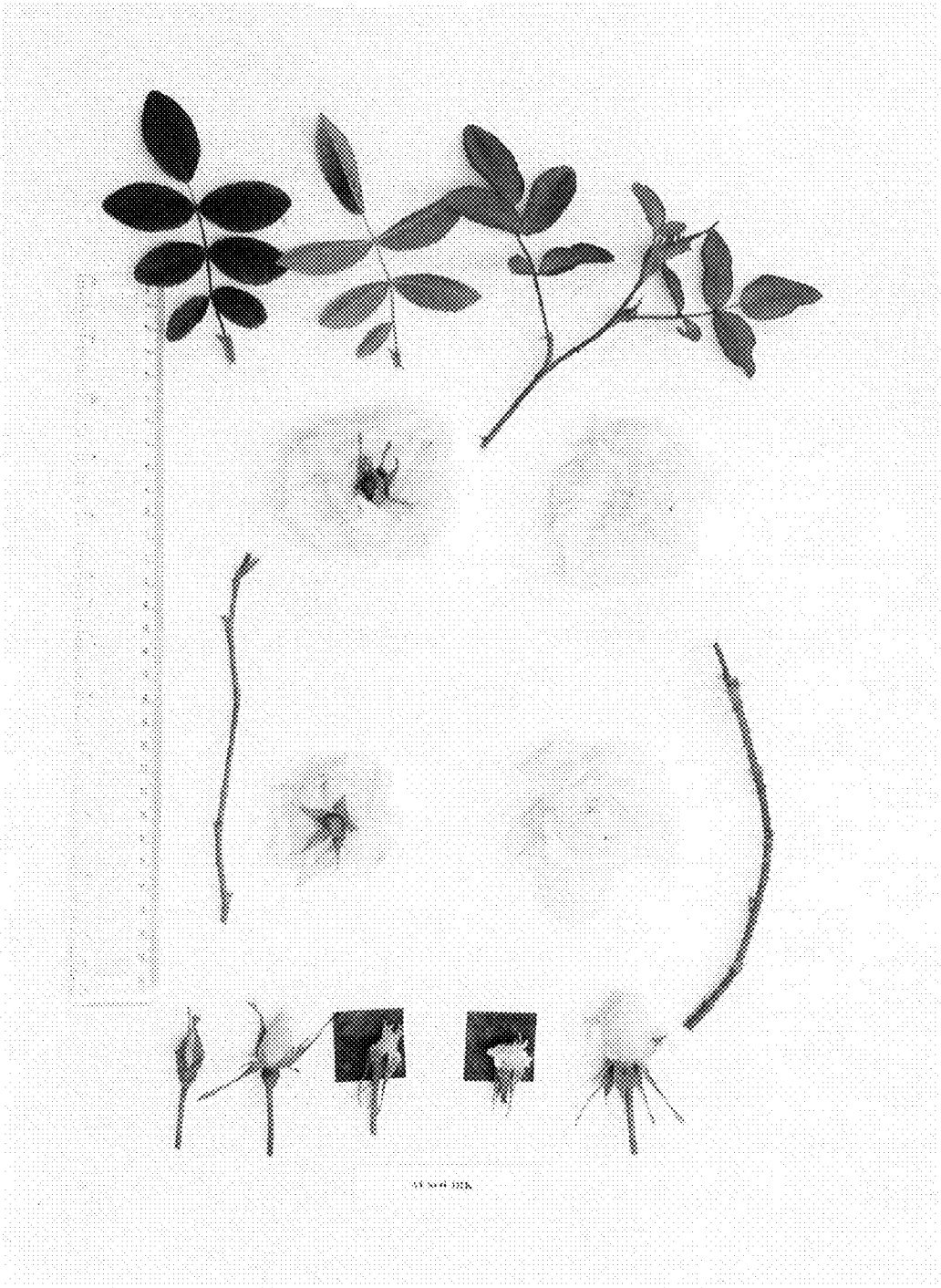

* * * * *